United States Patent [19]

Piontek et al.

[11] Patent Number: 5,658,253
[45] Date of Patent: Aug. 19, 1997

[54] STYLET DEVICE FOR GUIDING AN ENTERAL FEEDING TUBE

[75] Inventors: Carl Joseph Piontek, Powell, Ohio; Paul Allen Baker, Gainesville, Fla.

[73] Assignee: Abbott Laboratories, Abbott Park, Ill.

[21] Appl. No.: 392,015

[22] Filed: Feb. 21, 1995

[51] Int. Cl.$^6$ .................................................. A61M 25/00
[52] U.S. Cl. ........................ 604/170; 604/164; 604/165; 604/282; 128/657
[58] Field of Search ........................ 604/51, 164, 165, 604/170, 282; 128/657

[56] References Cited

U.S. PATENT DOCUMENTS

| | | | |
|---|---|---|---|
| 4,249,535 | 2/1981 | Hargest, III . | |
| 4,388,076 | 6/1983 | Waters | 604/170 X |
| 4,388,706 | 6/1983 | Butler . | |
| 4,496,347 | 1/1985 | MacLean et al. | 604/164 |
| 4,636,200 | 1/1987 | Vaillancourt | 604/170 |
| 4,826,485 | 5/1989 | Johnson | 604/170 |
| 4,850,983 | 7/1989 | Brenneman et al. | 604/170 X |
| 4,874,365 | 10/1989 | Frederick et al. | 604/165 X |
| 4,964,409 | 10/1990 | Tremulis | 128/657 |
| 5,030,204 | 7/1991 | Badger et al. | 128/657 X |
| 5,092,847 | 3/1992 | Pozzo | 604/170 |
| 5,190,528 | 3/1993 | Fonger et al. | 604/164 X |
| 5,209,734 | 5/1993 | Hurley et al. | 604/282 X |
| 5,242,389 | 9/1993 | Schrader et al. | 604/170 X |
| 5,382,234 | 1/1995 | Cornelius et al. | 604/282 X |
| 5,395,335 | 3/1995 | Jang | 604/164 X |
| 5,484,407 | 1/1996 | Osypka | 128/657 X |

*Primary Examiner*—Sam Rimell
*Assistant Examiner*—Robert V. Racunas
*Attorney, Agent, or Firm*—Brian R. Woodworth

[57] ABSTRACT

The present invention is an improved stylet for a enteric or nasoenteric feeding tubes. In broadest terms, the present invention comprises: a stylet for a feeding tube, the stylet having: (a) a stylet hub having a bore therethrough and adapted to be attached to one end of the feeding tube, the bore having an inner surface; (b) a longitudinally extending reinforcement member adapted to extend through the feeding tube, the reinforcement member having a proximal end; and (c) a hollow member having an outer surface and having an aperture, the hollow member disposed in the bore so as to hold the inlet end of the reinforcement member between the outer surface and the inner surface through an interference fit.

9 Claims, 3 Drawing Sheets

STYLET DEVICE FOR GUIDING AN ENTERAL FEEDING TUBE

TECHNICAL FIELD

This invention relates to a novel flow through stylet for use with enteral feeding tubes. The novel stylet comprises a hub which is attached to the stylet wire through a press interference fit of a hollow member.

BACKGROUND OF THE INVENTION

The use of a stiffening means or stylet within a flexible enteral feeding tube to stiffen the tubing so as to introduce the tubing into the correct location in a patient is known. To determine whether the tip of the feeding tube is properly positioned, the physician usually uses X-ray or other methods such as aspiration of gastric contents, called "residuals." It is conventional to remove the stylet after the tubing has been inserted into the patient. In the event that it is subsequently found that the tip of the tube has not been properly positioned, the stylet must be re-introduced into the tubing while in the patient. Such a procedure is risky since there is the possibility that the end of the stylet may protrude through the tubing and puncture soft gastrointestinal and/or respiratory tissues. Alternatively, the tube may be removed from the patient, with the stylet being re-inserted into the tubing outside the patient. Such a procedure causes discomfort in the patient and also requires more time, particularly if the procedure has to be repeated before the tube is lodged in the proper position.

U.S. Pat. No. 4,388,076 to Waters discloses a stylet design which features a reinforcement wire that is deformed at its attachment end to allow it to be secured in the stylet aperture or hub. This design has the disadvantage of requiring the attachment end of the reinforcement wire to be deformed in a separate operation before its assembly with the stylet hub.

U.S. Pat. No. 4,826,485 to Johnson discloses an invention intended to improve upon the invention of Waters. Its design allows the reinforcement wire to be located outside the stylet aperture. This is accomplished in the design of the Johnson patent by attaching the reinforcement wire in a separate aperture at a position offset from the hub's main aperture. However, this design is quite complex as it also requires that the attachment end of the reinforcement wire be deformed or shaped in order to be held in its separate aperture. Also, the stylet hub is itself of a complex design which requires two bores to accommodate the attachment end of the reinforcement wire and to form the main aperture.

It is therefore one aspect of the present invention to provide a stylet that allows the convenient aspiration of the gut without obstruction by the reinforcement wire.

It is also an aspect of the invention to provide a stylet design that is simpler to produce and that can be made of standard materials by convenient and cost effective procedures.

In light of the present disclosure and the practice of the present invention, other advantages and solutions to other problems will become apparent to one of ordinary skill in the relevant art.

DISCLOSURE OF THE INVENTION

The present invention relates to an improved stylet for an enteric or nasoenteric feeding tube. There is disclosed, in broadest terms, an invention which comprises a stylet for a feeding tube having two ends, comprising: (a) a stylet hub having a bore therethrough and adapted to be attached to one end of the feeding tube, the bore having an inner surface; (b) a longitudinally extending reinforcement member adapted to extend through the feeding tube, the reinforcement member having a proximal and a distal end, the proximal end being that end to which the stylet hub is attached; and (c) a hollow member having an outer surface and having an aperture, the hollow member disposed in the bore so as to hold the proximal end of the reinforcement member between the outer surface of the hollow member and the inner surface of the stylet hub through an interference fit, while facilitating the flow of a fluid through the stylet hub.

There is also disclosed an invention which comprises a stylet for a feeding tube having two ends, comprising: (a) a stylet hub having a centered bore therethrough, the centered bore having a longitudinal axis, and being adapted to be attached to one end of the feeding tube, the bore having an inner surface; (b) a longitudinally extending reinforcement member adapted to extend through the feeding tube, the reinforcement member having a proximal end; and (c) a hollow member having an outer surface and an aperture, the aperture having a longitudinal axis, with the hollow member disposed in the bore so as to hold the proximal end of the reinforcement member between the outer surface of the hollow member and the inner surface of the bore of the stylet hub through an interference fit while maintaining the longitudinal axis of the centered bore substantially parallel to the longitudinal axis of the aperture, and facilitating the flow of a fluid through the stylet hub.

It is preferred that the bore of the stylet hub and the aperture of the hollow member are substantially coaxial.

The stylet may be made of any appropriate material, but preferably should be a non-creeping polymeric material; that is, a material which when placed in an interference fit with the reinforcement member will not allow the reinforcement member to slip. Examples of such materials include polymeric materials, such as polycarbonates; as well as reinforced plastics and metals. Such materials should be capable of having sufficient hoop strength (i.e., the ability of a hoop-shaped body to resist forces directed outward from its center) to oppose the hollow member so that the stylet bore and hollow member are able to hold the inlet end of the reinforcement member between them. Of these materials, polycarbonate is preferred.

The reinforcement member may be any appropriately resilient but longitudinally stiff material capable of guiding the feeding tube into the patient once placed inside the feeding tube. Those skilled in the art will readily appreciate what materials may be used to produce a useful stylet. Appropriate materials include metal wire, braided or unbraided, such as stainless steel wire. The reinforcement member may also be any other material which is capable of functioning as described above, such as plastics or composite materials, such as metal-reinforced plastics. The hollow member may also be of any material of suitable for the purpose described. For instance, the hollow member may be a polymeric material such as those described above or, preferably, a metal cannnla such as those use in syringes, as they may be inexpensively obtained and possess the required physical properties.

Preferably, the bore comprises an abutment surface adapted to position the inlet end of the reinforcement member in the bore. This may be accomplished by constructing the bore so as to have two portions of different diameters (as shown in the accompanying drawings).

It is also preferred that the bore centered in the stylet hub and the aperture centered in the hollow member be provided such that, once the hollow member is positioned within the bore of the stylet hub, the longitudinal axis of the center bore of the stylet hub is co-axial with the longitudinal axis of the aperture in the hollow member.

Although offset from the longitudinal axis of the bore and aperture, the reinforcement member is sufficiently flexible so as to be coaxial with the feeding tube once it extends a short distance from the stylet hub.

One of the important features of the present invention is that it may be in place in a feeding tube while allowing for aspiration of stomach fluids to check for placement of the distal end of the feeding tube. This is particularly important for the removal of residuals from the gut, and for testing and monitoring the patient. Placed as it is, the reinforcement member does not interfere with the passage of fluids through the combined bore/aperture passageway. The non-removal of the reinforcement member allows the operator to conveniently reposition the tube if an attempt to remove residuals indicates the tube has been improperly placed.

Another very beneficial feature of the present invention is that it is of a simple and easy to produce construction. The costs associated with the production of a stylet according to this invention are less than the prior art flow through stylets.

The invention also includes a feeding tube having a stylet according to the present invention. Feeding tubes in accordance with known techniques, and of known designs and materials may be used.

DETAILED DESCRIPTION OF THE PREFERRED EMBODIMENT

In accordance with the foregoing summary of the invention, the following describes one embodiment of the present invention that is considered to be the preferred embodiment.

Figure 1:
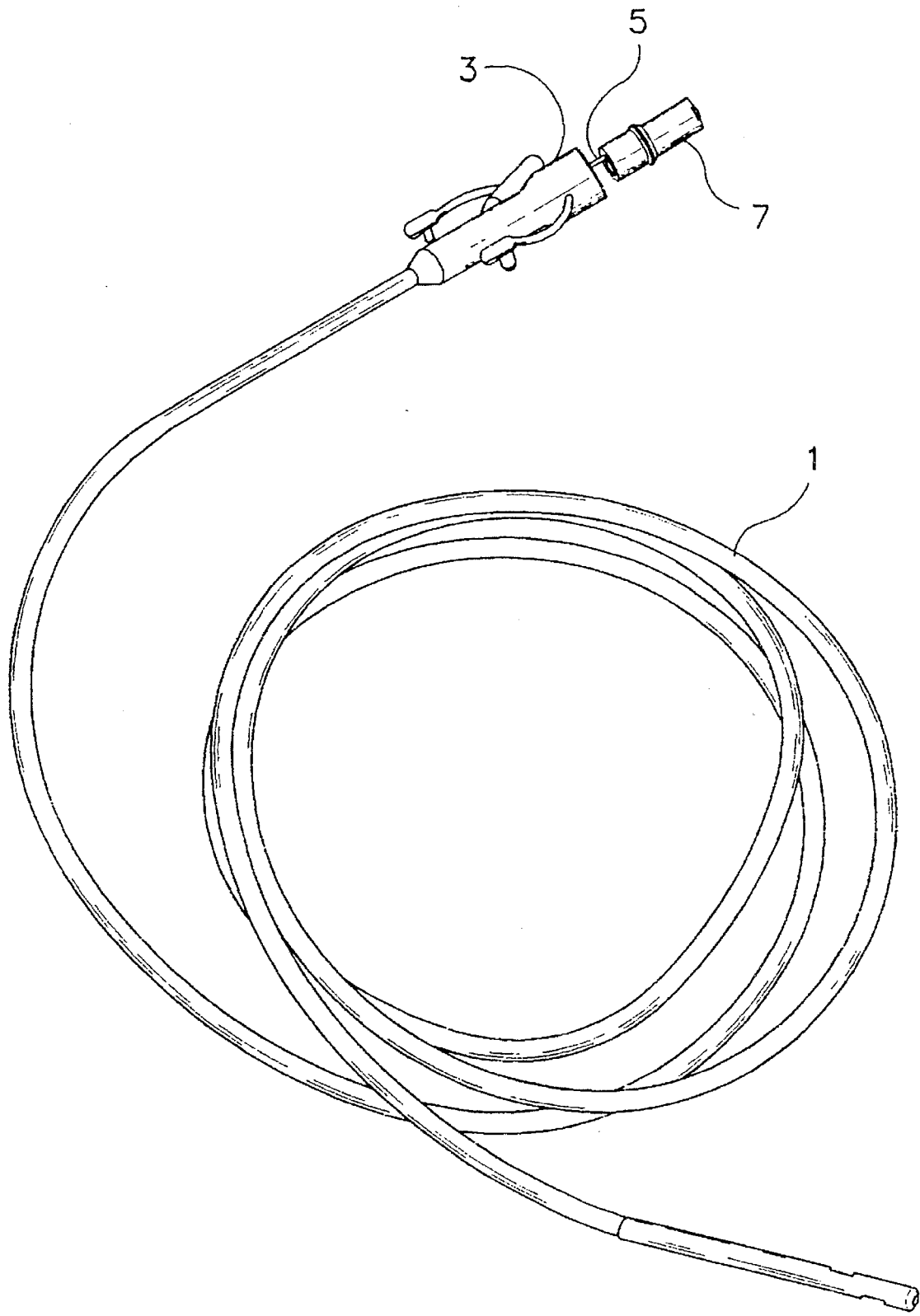
FIG. 1 is a perspective view of an enteral feeding tube in accordance with one embodiment of the present invention.

FIG. 1 shows enteral feeding tube 1 having proximal end fitting 3 attached to its proximal end. FIG. 1 also shows the reinforcement member 5, extending into feeding tube 1, and attached to stylet hub 7.

Figure 2:
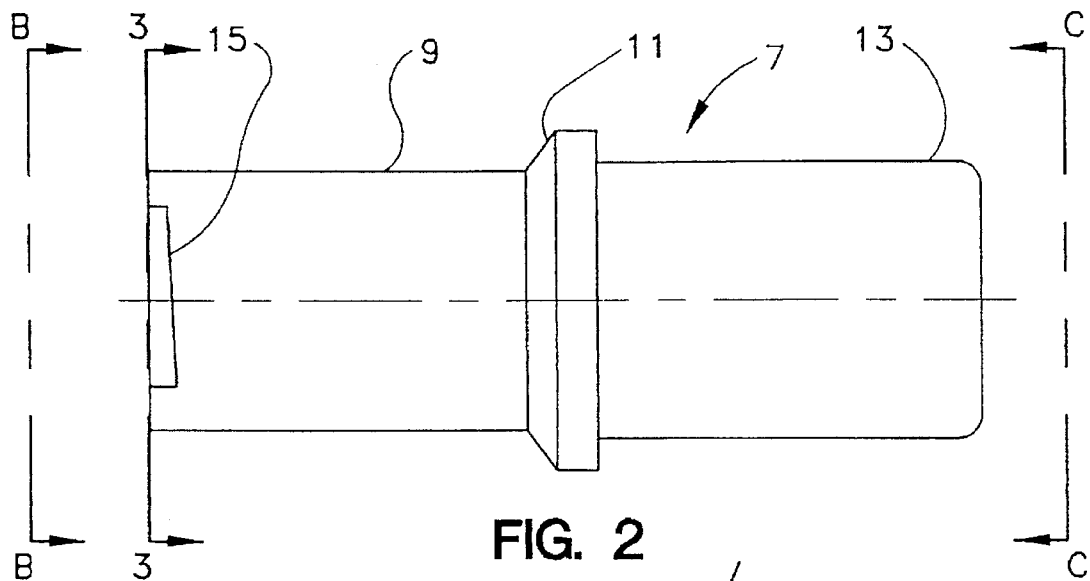
FIG. 2 is an elevational view of a stylet hub in accordance with one embodiment of the present invention.
Figure 3:
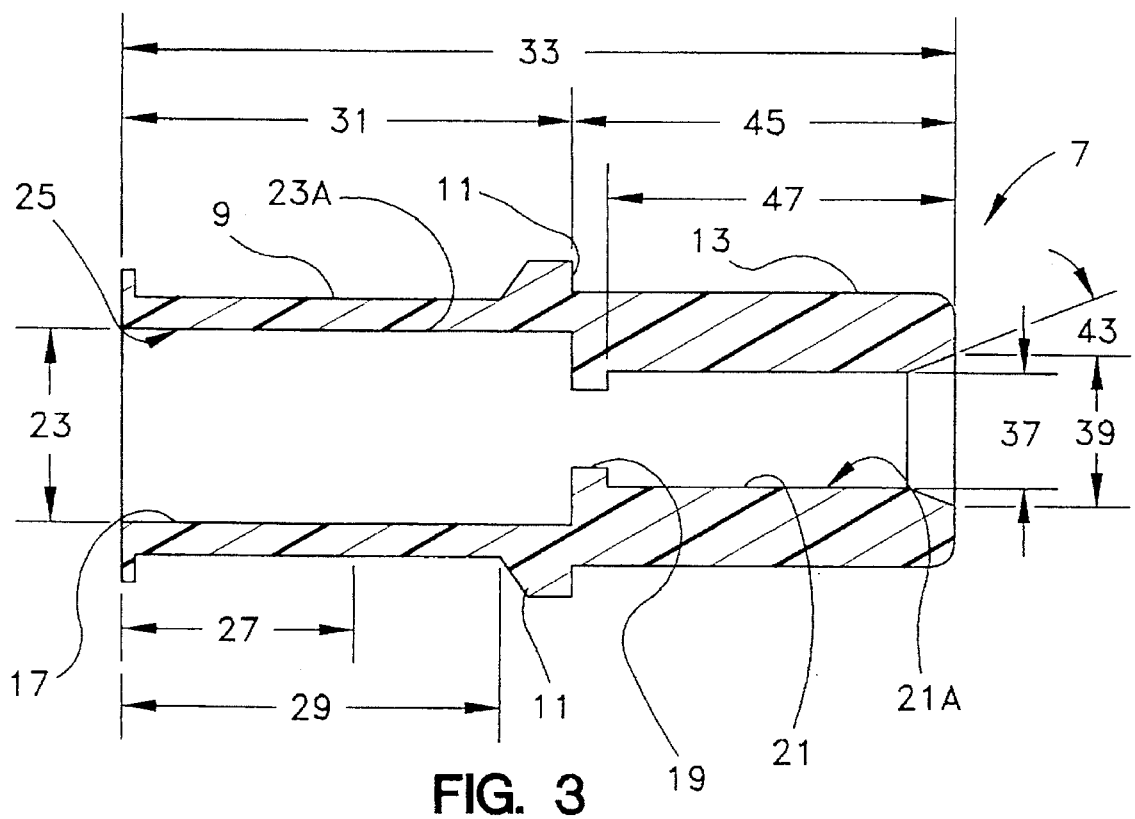
FIG. 3 is a cross-section of a stylet hub in accordance with one embodiment of the present invention, taken along line 3—3 of FIG. 2.

FIG. 2 shows stylet hub 7 having attachment end portion 9, abutment flange 11 and inlet end portion 13. Although not a limitation to the present invention, the stylet hub may have a length of about 0.900 inch (2.286 cm.) (dimension 33) as seen in FIG. 3. Attachment end portion 9 has attachment ears 15 (commonly referred to as a Luer Lock) for fastening to a liquid nutritional container or a syringe. Such attachment ears 15, which are common on medical devices, are typically tapered from 0.040 inch (0.102 cm.) down to 0.032 inch (0.08 cm.) thickness, and are approximately 0.156 inch (0.396 cm.) in length.

Figure 2A:
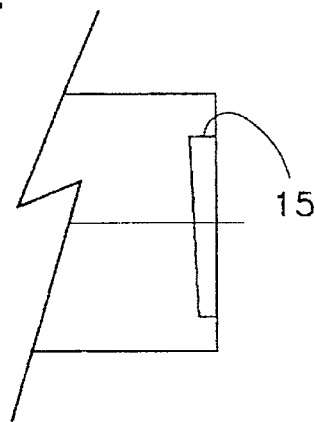
FIG. 2A is an elevational view of the opposing side of the attachment end of the stylet hub shown in FIG. 2.

FIG. 2A shows the opposing side of the attachment end portion 9 of the stylet hub shown in FIG. 2, showing the other attachment ear 15.

Figure 2B:
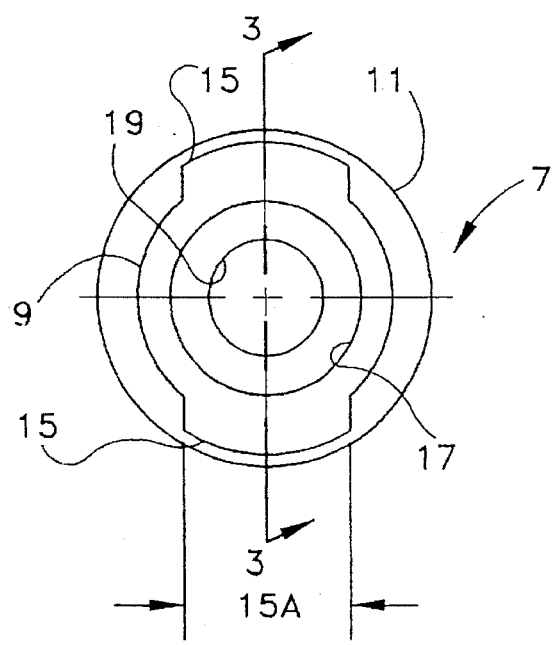
FIG. 2B is an elevational longitudinal view of the attachment end of the stylet hub shown in FIG. 2.

FIG. 2B shows an end-on view of the attachment end portion 9 (having a diameter of about 0.250 inch (0.635 cm.)) of the stylet hub 7 shown in FIG. 2. FIG. 2B also shows attachment bore 17 and intermediate bore 19. Flange 11 can also be seen in FIG. 2B. The diameter of flange 11 is about 0.390 inch (0.991 cm.). Also shown are attachment ears 15 which have a length 15A of 0.156 inch (0.396 cm.).

Figure 2C:
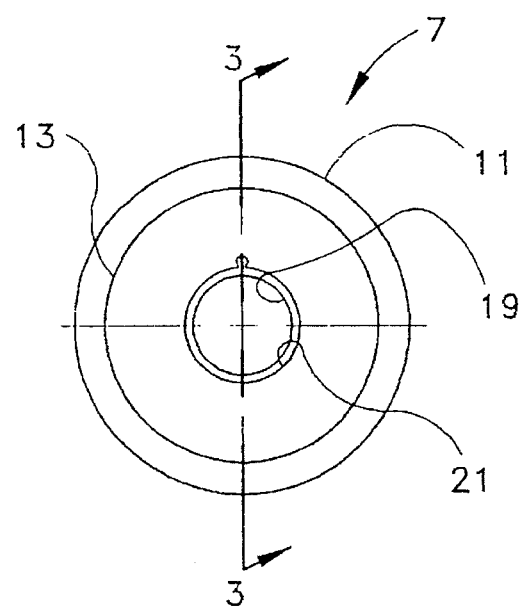
FIG. 2C is an elevational longitudinal view of the inlet end of the stylet hub shown in FIG. 2.

FIG. 2C shows an end-on view of the inlet end portion 13 of the stylet hub 7 shown in FIG. 2. FIG. 2B also shows inlet bore 21 and intermediate bore 19, as well as inlet end portion 13. Flange 11 can also be seen in FIG. 2C.

FIG. 3 is a cross-section along line 3—3 shown in FIGS. 2, 2B and 2C. FIG. 3 shows stylet hub 7 having attachment end portion 9, abutment flange 11 and inlet end portion 13. The length of inlet end portion is about 0.400 inch (1.016 cm.) (dimension 45). FIG. 3 also shows attachment bore 17, intermediate bore 19 and inlet bore 21. The inside diameter of attachment bore 17 is 0.170 inch (0.432 cm.) (dimension 23) and has a 0.060 inch (0.152 cm.) taper (shown at 25). The taper extends back from the end of attachment end portion 0.250 inch (0.635 cm.) (dimension 27). The inside diameter of the attachment bore beyond the taper (Dimension 23A) is about 0.156 inch (0.396 cm.) to about 0.158 inch (0.401 cm.). Dimensions 29 and 31 are 0.400 inch (1.02 cm.) and 0.500 inch (1.27 cm.), respectively. Inlet bore 21 has an inside diameter of 0.120 inch (0.305 cm.) (dimension 37) which tapers outward to a terminal diameter of 0.150 inch (0.31 cm.) (dimension 39), at an angle of about 20 degrees (angle 43). The total length of inlet bore 21 is about 0.350 inch (0.889 cm.) (dimension 47). Intermediate bore 19 has an inside diameter of about 0.090 inch (0.229 cm.).

Figure 4:
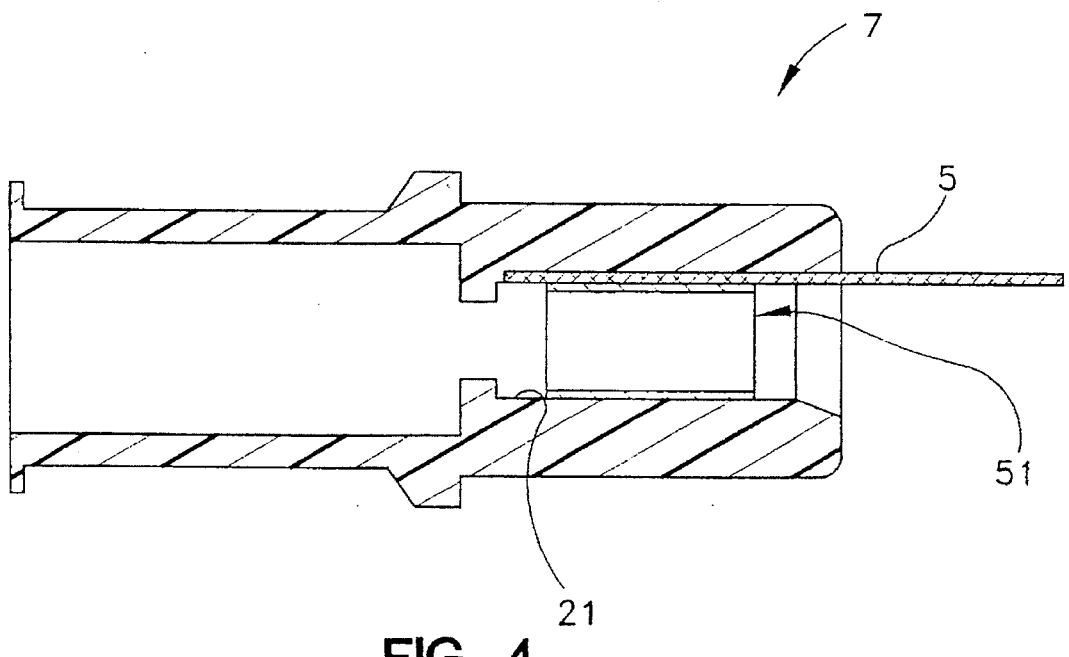
FIG. 4 is a cross-section of a stylet hub in accordance with one embodiment of the present invention, showing the position of the reinforcement member.

FIG. 4 shows a cross-section of stylet hub 7 as described in FIG. 3 and having reinforcement wire 5 held in inlet end bore 21 through a press interference fit with hollow member 51. Hollow member 51 has a inside diameter of 0.085 inch (0.216 cm.), an outside diameter of 0.108 inch (0.274 cm.) and a length of 0.200 inch (0.508 cm.).

In the described embodiment, the stylet hub 7 is of a polycarbonate material, such as MaKrolon® 2658-3129 resin, (white) commercially available from Miles Inc., Polymers Division, Mobay Road, Pittsburgh, Pa. 15205-9741. The radius on all sharp edges is about 0.03 inch (0.076 cm.) minimum. The stylet hub has a flash of 0.010 inch (0.0254 cm.) maximum, a parting line flash of 0.020 inch (0.0508 cm.) maximum and a parting line mismatch of 0.005 inch (0.0127 cm.) maximum. The gate remnantes are about 0.010 inch (0.0254 cm.) maximum. The hollow member 51 is of 302/304 stainless steel, typically about 0.035 inch (0.0889 cm.) to about 0.040 inch (0.102 cm.) in diameter. The pull-out force for the reinforcement member is about 10 lbs.

The reinforcement wire may be straight or braided.

In light of the foregoing disclosure, it will be within the ability of one skilled in the plastic and polymer extrusion and molding arts to make modifications to the present invention, such as through the substitution of equivalent parts, materials, or arrangement of parts, or the integration or disintegration of components, without departing from the spirit of the invention.

We claim:

1. A stylet for use with a feeding tube, said stylet comprising:

(a) a stylet hub defining a bore therethrough and constructed for attachment to one end of a feeding tube, said stylet hub having an inner surface;

(b) a longitudinally extending reinforcement member having a proximal end; and (c) a retaining member having an outer surface and defining an aperture therethrough, said retaining member disposed in said bore defined by said stylet hub, said proximal end of said reinforcement member disposed between said outer surface of said retaining member and said inner surface of said stylet hub, said retaining member outer wall and said inner surface of said stylet hub constructed to retain said reinforcement member therebetween through an interference fit.

2. A stylet according to claim 1 wherein said bore and said aperture are substantially coaxial.

3. A stylet according to claim 1 wherein said stylet hub is constructed of a non-creeping polymeric material.

4. A stylet according to claim 1 wherein said stylet hub is constructed of a material selected from a group consisting of polycarbonate polymers, metal-reinforced plastics, and metals.

5. A stylet according to claim 1 wherein said reinforcement member comprises a braided metal wire.

6. A stylet according to claim 1 wherein said reinforcement member is constructed of a plastic material.

7. A stylet according to claim 1 wherein said hollow member is constructed of a metal material.

8. A stylet for use with a feeding tube, said stylet comprising:

(a) a stylet hub defining an axial bore therethrough, said stylet hub having an inner surface;

(b) a longitudinally extending reinforcement member having a proximal end; and (c) a retaining member having an outer surface and defining an aperture therethrough, said retaining member coaxially disposed in said bore of said stylet hub, said proximal end of said reinforcement member disposed between said outer surface of said retaining member and said inner surface of said stylet hub, said outer surface of said retaining member and said inner surface of said stylet hub constructed to retain said proximal end of said reinforcement member through an interference.

9. An enteric feeding device comprising:

(a) a flexible tube having a proximal end and a distal end;

(b) a stylet hub defining a bore therethrough, said stylet hub removably secured to said proximal end of said tube;

(c) a reinforcement member having a proximal end, said reinforcement member dimensioned to extend through said tube; and (d) a retaining member having an outer surface and defining an aperture therethrough, said hollow member disposed in said bore defined by said stylet hub, said proximal end of said reinforcement member disposed between said stylet hub and said outer surface of said retaining member said stylet hub and said outer surface of said retaining member constructed to retain said retaining member therebetween through an interference fit.

* * * * *